United States Patent
Sabry et al.

(10) Patent No.: US 11,150,130 B2
(45) Date of Patent: Oct. 19, 2021

(54) COMPACT MULTI-PASS GAS CELL FOR MULTI-GAS SPECTRAL SENSORS

(71) Applicant: Si-Ware Systems, Cairo (EG)

(72) Inventors: Yasser M. Sabry, Cairo (EG); Mohammad Sakr, Cairo (EG); Bassam A. Saadany, Cairo (EG); Momen Anwar, Cairo (EG); Mohamed H. Al Haron, Cairo (EG)

(73) Assignee: SI-WARE SYSTEMS, Cairo (EG)

( * ) Notice: Subject to any disclaimer, the term of this patent is extended or adjusted under 35 U.S.C. 154(b) by 0 days.

(21) Appl. No.: 16/808,238

(22) Filed: Mar. 3, 2020

(65) Prior Publication Data

US 2020/0284654 A1  Sep. 10, 2020

Related U.S. Application Data

(60) Provisional application No. 62/813,714, filed on Mar. 4, 2019.

(51) Int. Cl.
*G01J 3/02* (2006.01)
*G01J 3/08* (2006.01)
(Continued)

(52) U.S. Cl.
CPC ............. *G01J 3/021* (2013.01); *G01J 3/0208* (2013.01); *G01J 3/0262* (2013.01); *G01J 3/08* (2013.01);
(Continued)

(58) Field of Classification Search
CPC .................................................... G01N 21/031
See application file for complete search history.

(56) References Cited

U.S. PATENT DOCUMENTS

| | | | |
|---|---|---|---|
| 3,861,809 A | 1/1975 | Hall | |
| 5,009,493 A * | 4/1991 | Koch | G01N 21/031 |
| | | | 356/246 |

(Continued)

FOREIGN PATENT DOCUMENTS

| | | |
|---|---|---|
| DE | 10216047 A1 | 10/2003 |
| FR | 2767195 A1 | 2/1999 |
| GB | 2316172 A | 2/1998 |

OTHER PUBLICATIONS

PCT/US2020/020962. Int'l Search Report & Written Opinion (dated Jun. 19, 2020).

(Continued)

*Primary Examiner* — Shawn Decenzo
(74) *Attorney, Agent, or Firm* — Loza & Loza, LLP; Holly L. Rudnick

(57) ABSTRACT

Aspects of the disclosure relate to a multi-pass gas cell that includes a set of two or more reflectors, an input collimating optical component, and an output focusing optical component. The input and output optical components are integrated with at least one of the two or more reflectors. For example, the input and output optical components may be integrated on opposite ends of a single one of the reflectors or may be integrated on the same end of a single reflector. The input and output optical components may further be integrated with different reflectors. In some examples, the set of reflectors and optical components may be fabricated within the same substrate.

31 Claims, 15 Drawing Sheets

(51) Int. Cl.
*G01J 3/10* (2006.01)
*G01N 33/00* (2006.01)

(52) U.S. Cl.
CPC ............ *G01J 3/10* (2013.01); *G01N 33/0009* (2013.01); *G01J 2003/102* (2013.01)

(56) References Cited

U.S. PATENT DOCUMENTS

| | | | | |
|---|---|---|---|---|
| 5,125,742 | A | 6/1992 | Wilks, Jr. | |
| 5,835,231 | A * | 11/1998 | Pipino | G01N 21/552 356/440 |
| 6,486,474 | B1 * | 11/2002 | Owen | G01N 21/031 250/339.02 |
| 9,250,175 | B1 * | 2/2016 | McManus | G01N 21/031 |
| 10,113,957 | B1 * | 10/2018 | Yi | G01N 21/47 |
| 2007/0279633 | A1 * | 12/2007 | Yi | G01N 21/61 356/432 |
| 2011/0164251 | A1 * | 7/2011 | Richter | G01N 21/031 356/440 |
| 2012/0092782 | A1 * | 4/2012 | So | G01N 21/031 359/858 |
| 2012/0242989 | A1 * | 9/2012 | So | G02B 5/10 356/402 |
| 2015/0062572 | A1 * | 3/2015 | Tharaldsen | G01N 21/31 356/300 |
| 2015/0083918 | A1 * | 3/2015 | Emmenegger | G01N 21/3504 250/341.1 |
| 2015/0260695 | A1 * | 9/2015 | Spartz | G01N 30/8606 250/339.01 |
| 2017/0139182 | A1 * | 5/2017 | Sawyers | G02B 5/10 |
| 2017/0168275 | A1 * | 6/2017 | Akamatsu | G02B 17/0636 |
| 2017/0241904 | A1 * | 8/2017 | Barritault | G01N 21/3504 |
| 2019/0113442 | A1 * | 4/2019 | Shibuya | G01N 21/59 |

OTHER PUBLICATIONS

Colomb et al., "Screening volatile organic compounds (VOCs) emissions from five marine phytoplankton species by head space gas chromatography/mass spectrometry./"(HS-GC/MS). J. Environ. Monit. 10, 325-330 (2008).
Yokelson et al. "Trace gas measurements in nascent, aged, and cloud-processed smoke from African savanna fires by airborne Fourier transform infrared spectroscopy (AFTIR)." J. Geophys. Res. Atmos. 108 (2003).
Gao et al. "Detection of Ethanol Using a Tunable Interband Cascade Laser at 3.345µm." Photonic Sensors, 8, 303-309 (2018).
Hirschmann et al. "Sub-ppb detection of formaldehyde with cantilever enhanced photoacoustic spectroscopy using quantum cascade laser source." Appl. Phys. B, 111, 603-610(2013).
Eltagoury et al. "All-Silicon Double-Cavity Fourier-Transform Inared Spectrometer On-Chip." Adv. Mater. Technol. 4(10) 1900441 (2019).
Erfan et al. "On-Chip Micro-Electro-Mechanical System Fourier Transform Infrared (MEMS FT-IR) Spectrometer-Based Gas Sensing." Appl. Spectrosc. (2016).
Othman et al. "EXPRESS: Micro-Electro-Mechanical Fourier Transform Infrared (MEMS FT-IR) Spectrometer Under Modulated-Pulsed Light Source Excitation." Appl. Spectroscopy 0003702819886091 (2019).
Kraft et al. "MEMS-based compact FT-Spectrometers—A platform for spectroscopic mid-infared sensors." Proceedings of the Proceedings of IEEE Sensors (2008).
Briand et al. "Gas detection using a micromachined FTIR spectrometer." Proceedings of the Sensors 2007, pp. 1364-1367 (2007).
White. "Long Optical Paths of Large Aperture;" J. Opt. Soc. Am. 32, 285-288 (1942).
Hanst et al. "Spectroscopic Methods for Air Pollution Measurement." Advances in Environmental Science and Technology, J. N. Pitts and R. L. Metcalf, Eds. (Wiley, New York), p. 91-95 (1971).
Baumer. "Handbook of Plastic Optics." Wiley-VCH, 2nd edition (2010).

* cited by examiner

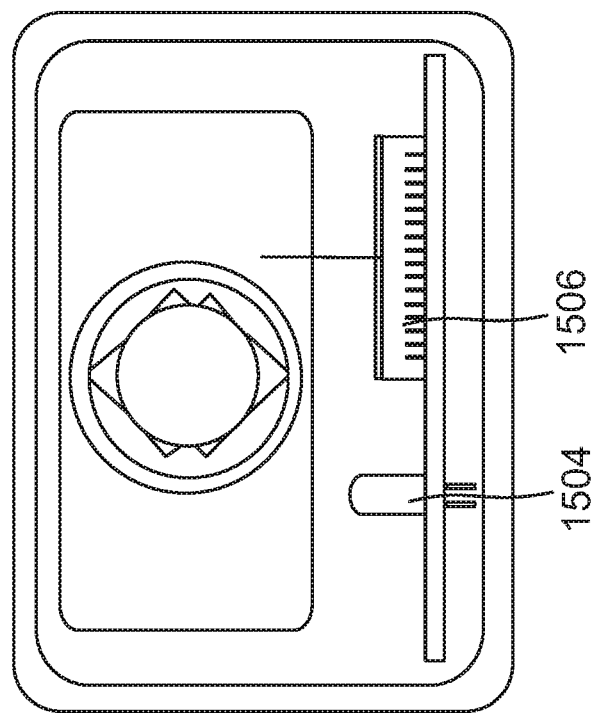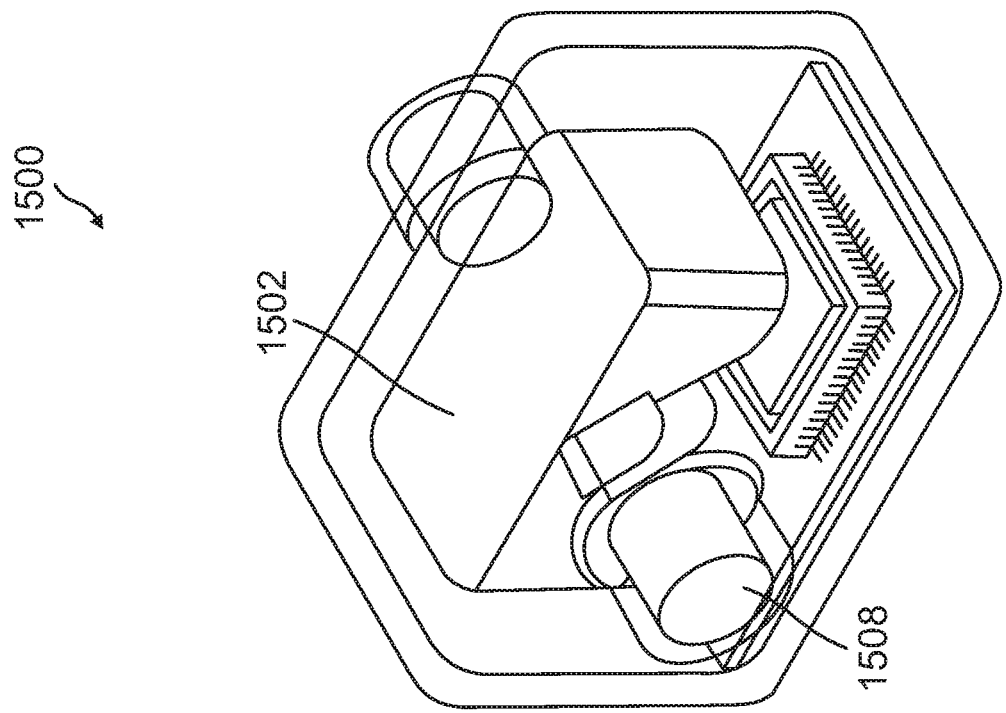
FIG. 15

COMPACT MULTI-PASS GAS CELL FOR MULTI-GAS SPECTRAL SENSORS

PRIORITY CLAIM

This application claims priority to and the benefit of Provisional Application No. 62/813,714, filed in the U.S. Patent and Trademark Office on Mar. 4, 2019, the entire content of which is incorporated herein by reference as if fully set forth below in its entirety and for all applicable purposes.

TECHNICAL FIELD

The technology discussed below relates generally to multi-pass optical gas cells, and in particular to the use of multi-pass optical gas cells with spectrometers, such as Micro-Electro-Mechanical-Systems (MEMS) spectrometers, within gas analyzers.

BACKGROUND

Various mechanisms may be used for gas analysis, such as gas chromatography, mass spectrometers, spectrometers, tunable diode laser spectrometer (TDLS), and photoacoustic-based TDLS. Among spectroscopy techniques, Fourier Transform Infrared (FTIR) provides a wide spectral range, along with the capability to analyze multiple gases simultaneously. The use of a MEMS spectrometer can also lead to a compact and inexpensive gas analyzer. Such MEMS-based FTIR spectrometers have been successful in measuring $C_2H_2$ with a detection limit of 350 ppm and $CO_2$ with a detection limit of 1800 ppm when coupled to a gas cell of 10 cm length. FTIR spectrometers that utilize a translation MEMS mirror with other discrete optical components have also been used to measured propane and butane for a path length of 6 cm. Other gas analyzer configurations have included MEMS lamellar grating FTIR spectrometers and MEMS based tunable filters with a swept laser source.

The gases inside a gas cell may be detected by sending light through the gas cell. A portion of the light will be absorbed by the gases, while the rest may be detected, for example, by a MEMS spectrometer. Some gas cells use a set of mirrors to reflect the light through multiple passes until the light exits the gas cell. The mirrors may have different designs, such as spherical, elliptical, or circular section cylinder mirrors. The reflecting surfaces of the gas cell may also take the form of opposed parabolic or parallel pairs, or may have a combination of flat, cylindrical, circular, spiral, or right circular cylinder arrangement of the multiple reflecting surfaces. Examples of gas cells may include, but are not limited to, White gas cells and Hanst gas cells. White gas cells reimage the source after each double pass of light up and down the cell, which confines the energy in the cell until the light exits. Due to the confinement, the only source of loss is the non-ideal reflectivity of the mirrors.

Increasing the number of passes results in increasing light absorption by the gas. As the light absorption increases, low gas concentrations become easier to detect. However, the throughput of the gas analyzer system decreases due to the reflection losses. This tradeoff typically produces an optimum point in the total path length that the light travels inside the gas cell. However, since gases may vary in concentration (or in absorption cross section), different path lengths may be needed for each range of concentration. For example, path lengths that are too long may saturate the gases with relative high concentrations, resulting in their lines disappearing in the absorption spectrum. Therefore, more than one gas cell or a gas cell with variable path length that is adjusted manually may be used to monitor more than one gas. Adding gas cells increases the cost, while manual adjustment increases the time involved in measuring the different gases.

Moreover, although gas analyzers with MEMS spectrometers have resulted in miniaturization of these devices, further miniaturization of the gas cells themselves may increase compatibility with MEMS technology and enable mass production.

SUMMARY

The following presents a summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a form as a prelude to the more detailed description that is presented later.

Various aspects of the disclosure provide a multi-pass gas cell that includes a set of two or more reflectors, an input collimating optical component, and an output focusing optical component, where the input and output optical components are integrated with at least one of the two or more reflectors. In some examples, the input and output optical components may include curved mirrors or lenses. In some examples, the set of two or more reflectors may include spherical mirrors, concave mirrors, flat mirrors, or cylindrical mirrors.

In one example, the set of two or more reflectors includes three spherical mirrors, each including a same radius of curvature that is equal to a distance between a first spherical mirror on one side of the multi-pass gas cell and each of second and third spherical mirrors on the other side of the multi-pass gas cell. The first spherical mirror has a length that is greater than the respective lengths of either of the second or third spherical mirrors. In some examples, the input and output optical components are integrated on opposite ends of the first spherical mirror. In other examples, the input and output optical components are integrated on the same end of the first spherical mirror. In this example, the larger spherical mirror may include an asymmetrical portion on the end opposite the end containing the input and output optical components to enable reflection of the collimated light back into the multi-pass cell at the point the light would normally exit the multi-pass cell.

In still other examples, the input and output optical components are integrated on opposite ends of the first spherical mirror, and an additional input optical component is integrated on the same end of the first spherical mirror as the other input optical component. In this example, each of the input optical components is optically coupled to receive a respective input beam (e.g., input light) and configured to direct respective collimated light along a different multi-pass optical path length. The different multi-pass optical path lengths may be realized by a discontinuity in one of the smaller spherical mirrors that results in a tilt between respective parts of the smaller spherical mirror formed by the discontinuity. The different multi-pass optical path lengths may produce different numbers of reflections of the respective collimated light. In some examples, the multi-pass gas cell may further include a switch configured to switch between two different light sources, each providing respective input light to one of the two input optical components.

In another example, the set of two or more reflectors may include a set of two concave mirrors, where a first concave mirror has a first radius of curvature and a second concave mirror has a second radius of curvature that is twice that of the first radius of curvature. A distance between the concave mirrors is equal to the second radius of curvature. In this example, an absorber may be inserted into the multi-pass gas cell to prevent stray light from reaching the optical output of the multi-pass gas cell.

In another example, the set of two or more reflectors may include at least four mirrors. The input optical component may be integrated with a first mirror and the second optical component may be integrated with a second mirror. The first and second mirrors may have a first length that is less than the length of the remaining mirrors. The input optical component may be integrated on a top portion of the first mirror to direct collimated light towards the second mirror at an angle selected to produce a spiral multi-pass optical path between the mirrors. The output optical component may integrated on a bottom portion of the second mirror to receive the output light reflected from the first mirror and to focus the output light towards the optical output of the multi-pass gas cell.

In another example, the set of two or more reflectors may include two flat mirrors. The input optical component is integrated with a first flat mirror and the output optical component is integrated with the second flat mirror. The multi-pass gas cell further includes a first optical Bessel component optically coupled to receive the collimated input light from the input optical component configured to generate input Bessel beams for propagation inside the multi-pass gas cell to produce multiple reflections thereof between the two flat mirrors. The multi-pass gas cell further includes a second optical Bessel component optically coupled to receive output Bessel beams resulting from the multiple reflections and configured to generate output collimated light towards the output optical component. In some examples, the first and second optical Bessel component may include axicon lenses, annular apertures, or conical reflectors.

In some examples, the multi-pass gas cell may include an enclosure configured to receive a gas, where the enclosure includes the set of reflectors and the input and output optical components. For example, the enclosure, set of reflectors and input and output optical components may be fabricated within the same substrate using injection molded optics. In some examples, a spectrometer and a light source may further be assembled inside the enclosure. In addition, the enclosure may include a circulation unit configured to circulate the gas from outside the enclosure to inside the enclosure. The enclosure may further include an element configured to absorb or block water content in the gas.

These and other aspects of the invention will become more fully understood upon a review of the detailed description, which follows. Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

BRIEF DESCRIPTION OF THE DRAWINGS

FIG. 15 is a diagram illustrating an exemplary optical mold including a multi-pass gas cell.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Figure 1:
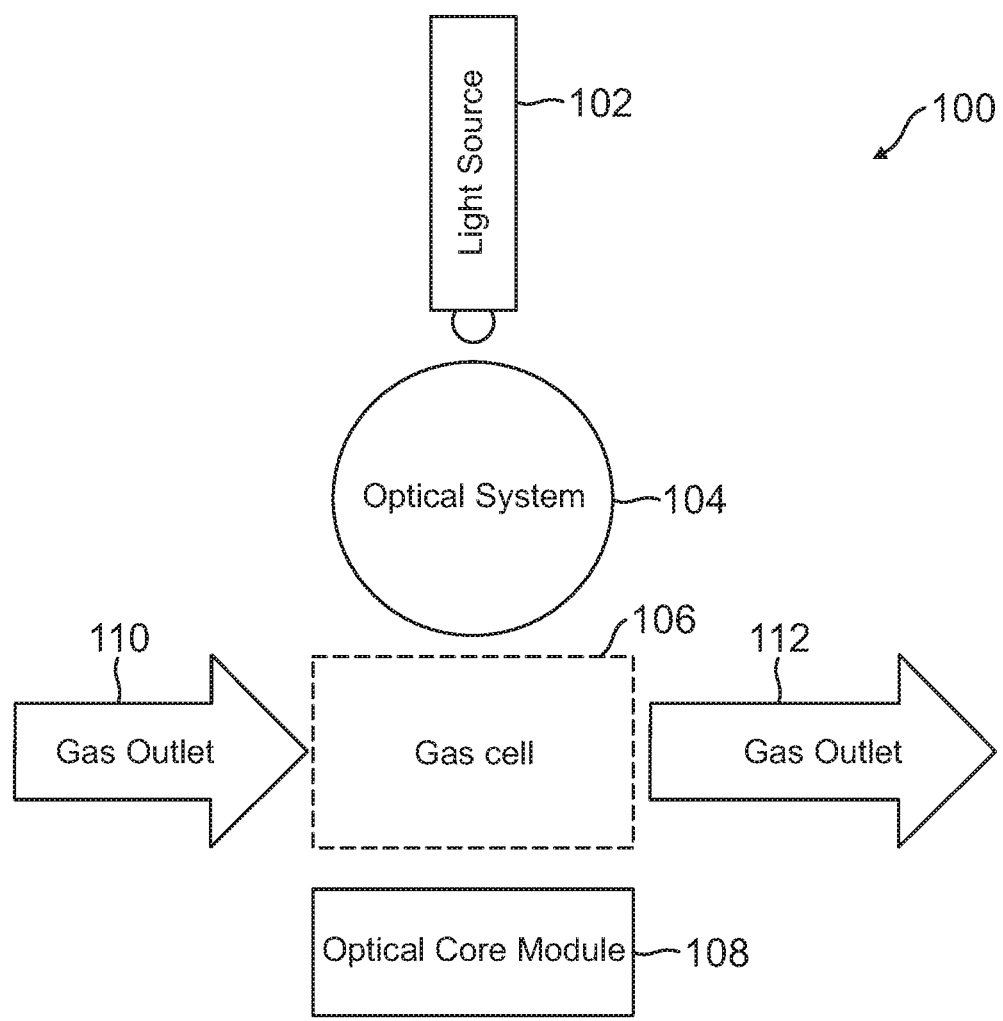
FIG. 1 is a diagram illustrating an example of a gas analyzer including a multi-pass gas cell.

FIG. 1 illustrates an example of a gas analyzer 100 including a light source 102, an optical system 104, a multi-pass gas cell 106, and an optical core module 108. The optical system 104 may include one or more optical components for enhancing the illumination of the light source 102. Gas may enter the multi-pass gas cell 106 via a gas inlet 110 and may exit the multi-pass gas cell 106 via a gas outlet 112. The gases inside the multi-pass gas cell may be detected by directing light from the light source 102 into the multi-pass gas cell 106 via the optical system 104. A portion of the light may be absorbed by the gases, while the remainder of the light may be detected by the optical core module 108.

The optical core module 108 may include, for example, a spectrometer and a detector. For example, the spectrometer may include an FTIR spectrometer configured to produce an interferogram that may be detected by the detector. The output of the detector may be processed to obtain the spectrum of the detected light, which may then be utilized to identify the gas or obtain other parameters associated with the gas, such as the concentration of the gas, the energy content in the gas, the total volatile organic compound, the amount of particulate matter in the gas, or other suitable parameter.

In some examples, the spectrometer and detector may be implemented on a Micro-Electro-Mechanical-Systems (MEMS) chip. As used herein, the term MEMS refers to the integration of mechanical elements, sensors, actuators and electronics on a common silicon substrate through microfabrication technology. For example, the microelectronics are typically fabricated using an integrated circuit (IC) process, while the micromechanical components are fabricated using compatible micromachining processes that selectively etch away parts of the silicon wafer or add new structural layers to form the mechanical and electromechanical components. One example of a MEMS element is a micro-optical component having a dielectric or metallized surface working in a reflection or refraction mode. Other examples of MEMS elements include actuators, detector grooves and fiber grooves.

The MEMS spectrometer of the optical core module 108 may include one or more micro-optical components (e.g., one or more reflectors or mirrors) that may be moveably controlled by a MEMS actuator. In some examples, the MEMS spectrometer may be fabricated using a Deep Reactive Ion Etching (DRIE) process on a Silicon On Insulator (SOI) wafer in order to produce the micro-optical components and other MEMS elements that are able to process free-space optical beams propagating parallel to the SOI substrate.

The multi-pass gas cell 106 may include a set of two or more reflectors configured to reflect the light through multiple passes within the gas cell 106 until the light exits the gas cell 106. In various aspects of the disclosure, the multi-pass gas cell 106 may be designed to be compatible with MEMS technology and mass production. In some examples, the multi-pass gas cell 106 may include optical components that facilitate compatibility with MEMS spectrometers. In addition, the multi-pass gas cell 106 may provide two or more multi-pass optical path lengths to enable measuring more than one gas, each with a different absorption.

Figure 2:
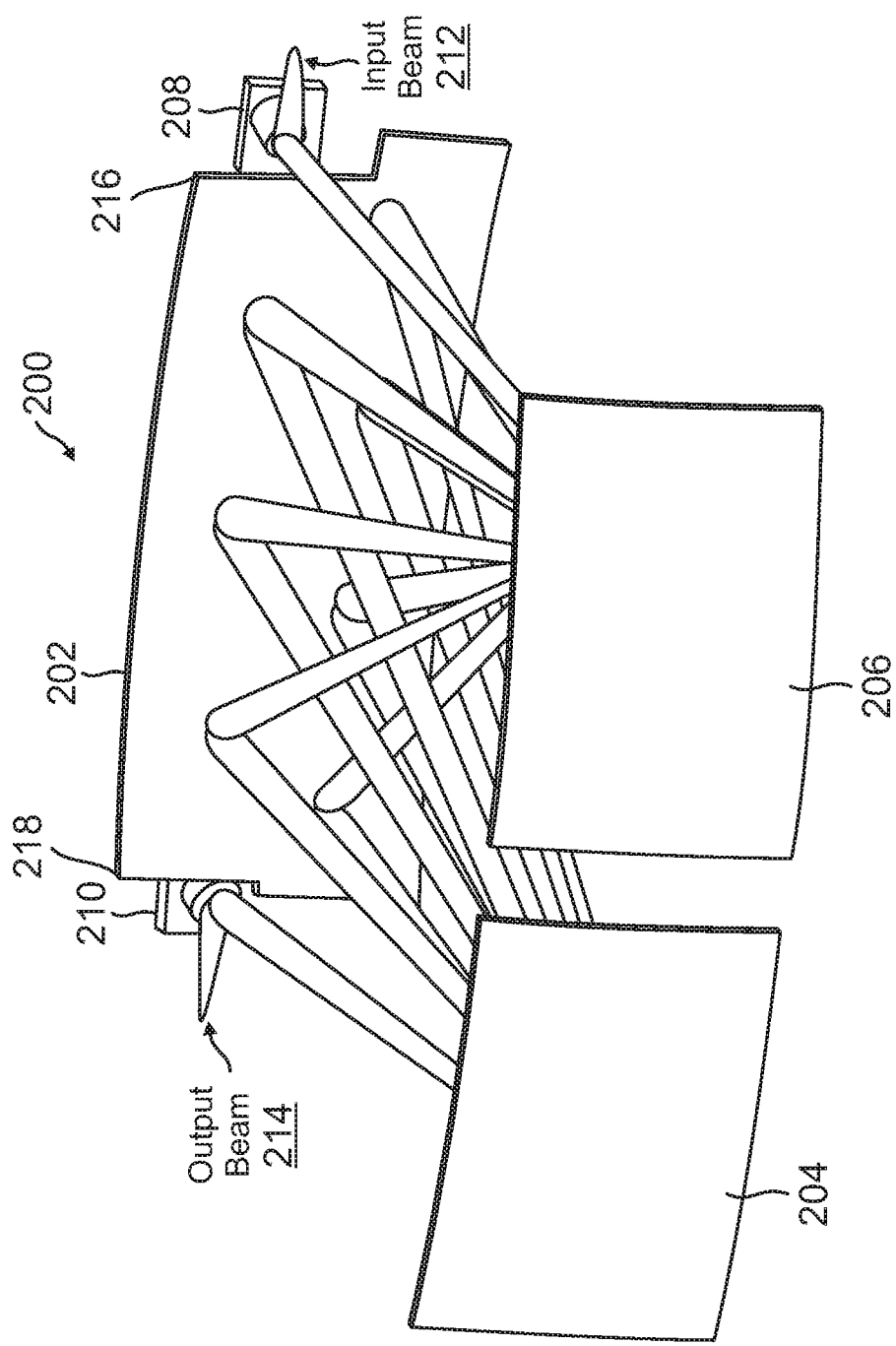
FIG. 2 is a diagram illustrating an example of a multi-pass gas cell including integrated collimating and focusing optical components.

FIG. 2 is a diagram illustrating an example of a multi-pass gas cell 200 in accordance with aspects of the disclosure. The multi-pass gas cell 200 includes a set of three reflectors 202, 204, and 206. In the example shown in FIG. 2, each reflector 202, 204, and 206 is a spherical mirror. Each of the spherical mirrors 202, 204, and 206 has the same radius of curvature that is equal to the separation (distance) between a larger spherical mirror 202 on one side of the gas cell 200 and two smaller spherical mirrors 204 and 206 on the other side of the gas cell 200. As shown in FIG. 2, spherical mirror 202 has a length that is greater than the respective lengths of either of spherical mirrors 204 and 206. For example, the longer spherical mirror 202 may have a length that is slightly less than twice the length of either of the shorter mirrors 204 and 206. In an example, the longer mirror may have a length of 180 mm, while each shorter mirror 204 and 206 may have a length of 100 mm. As such, the ratio between the length of the larger mirror 202 and a shorter mirror 204 or 206 may be 1.8. In addition, spherical mirrors 204 and 206 are tilted with respect to one another to provide a small angle between the mirrors 204 and 206 selected to maintain the light within the multi-pass gas cell 200. In some examples, the angle between the mirrors 204 and 206 may range between one and five degrees.

The multi-pass gas cell 200 further includes a first optical component 208 integrated with the spherical mirror 202 on a first end 216 thereof and a second optical component 210 integrated with the spherical mirror 202 on a second end 218 thereof opposite the first end 216. As used herein, the term "integrated" means that the components are collectively formed of and result in a solid piece of material (e.g., metal, glass, plastic, dielectric, semiconductor substrate, ceramic, etc.). In some examples, the first optical component 208 and the second optical component 210 each include curved mirrors or lenses. For example, the first optical component 208 and the second optical component 210 may include off-axis parabolic mirrors.

Reflectivity of the mirrors 202, 204, 206, 208, and 210 is determined mainly by the mirror fabrication technology and materials used in manufacturing. In some examples, the mirrors 202, 204, 206, 208, and 210 include a metallic coating that produces mirrors with high reflectivity and wide band response. In other examples, the mirrors 202, 204, 206, 208, and 210 may be dielectric mirrors (e.g., Bragg mirrors) composed of multiple thin layers of dielectrics. The number of dielectric layers and their thicknesses are designed to achieve specified reflectivity at different wavelengths. Dielectric mirrors may have higher reflectivity compared to the metallic mirrors. However, dielectric mirrors may not provide ultra-high reflectivity over a wide wavelength range.

In an aspect of the disclosure, each of the spherical mirrors 202, 204, and 206 has a constant thickness (e.g., around 5 mm to around 10 mm) to facilitate mass production of the multi-pass gas cell 200 using, for example, injection molded optics technology. Injection molding allows each of the mirrors 202, 204, 206, 208, and 210 of the multi-pass gas cell 200 to be fabricated in a self-aligned manner in a mass production environment. In addition, the two off-axis parabolic mirrors 208 and 210 may provide compatibility with MEMS spectrometers for miniature gas analyzer applications.

Figure 3:
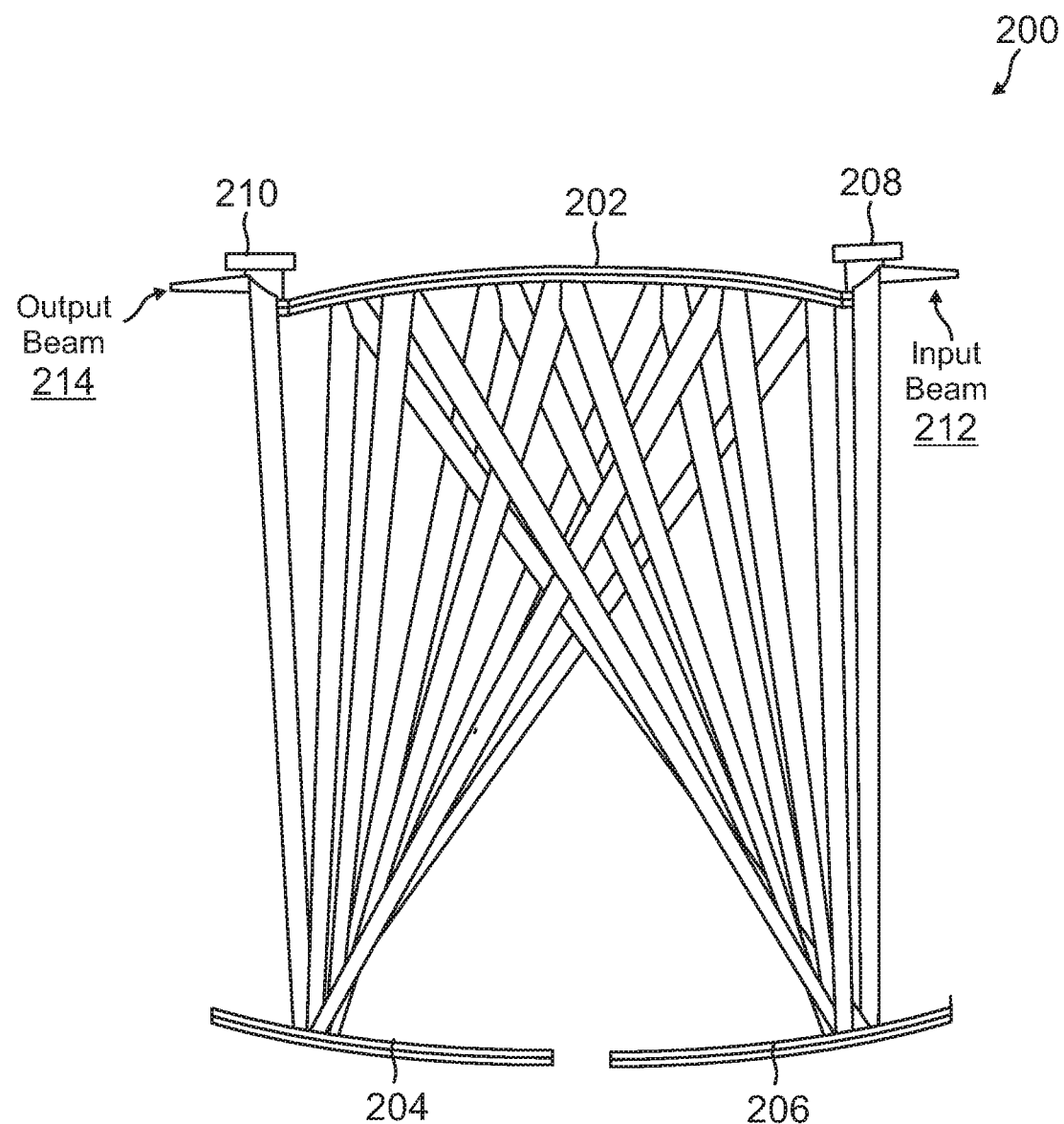
FIG. 3 is a diagram illustrating an elevation view of the multi-pass gas cell of FIG. 2.

As can be seen in FIG. 2 and the elevation view of the multi-pass gas cell 200 shown in FIG. 3, the off-axis parabolic mirror 208 positioned at an optical input of the multi-pass gas cell 200 is optically coupled to receive an input beam (e.g., input light) 212. In some examples, the input light 212 may be generated, for example, by a miniature light source (e.g., a light-emitting diode (LED) or filament source). The off-axis parabolic mirror 208 is configured to collimate the input light 212. In some examples, the parabola has the shape of an ideal collimator, and as such, the collimation is not accompanied with any spherical aberration. In addition, the off-axis parabolic mirror 208 may be a metallic mirror that has a very wide band reflectivity over the infrared (IR) range. Therefore, the collimation may also not experience any chromatic aberration.

The off-axis parabolic mirror 208 is further configured (or oriented within the gas cell 200) to direct the resulting collimated light (e.g., parallel rays) towards the spherical mirror 206, where the collimated light is reflected back towards the spherical mirror 202. Multiple reflections of the collimated light between the longer spherical mirror 202 and each of the shorter spherical mirrors 204 and 206 may then occur making at least two passes up and down the multi-pass gas cell 200. The off-axis parabolic mirror 210 is optically coupled to receive an output beam (e.g., output light) resulting from (e.g., after completing) the multiple reflections and is configured (or oriented within the gas cell 200) to focus the output light towards an optical output of the gas cell. For example, the optical output may be optically coupled to a spectrometer, such as a MEMS spectrometer.

Figure 4:
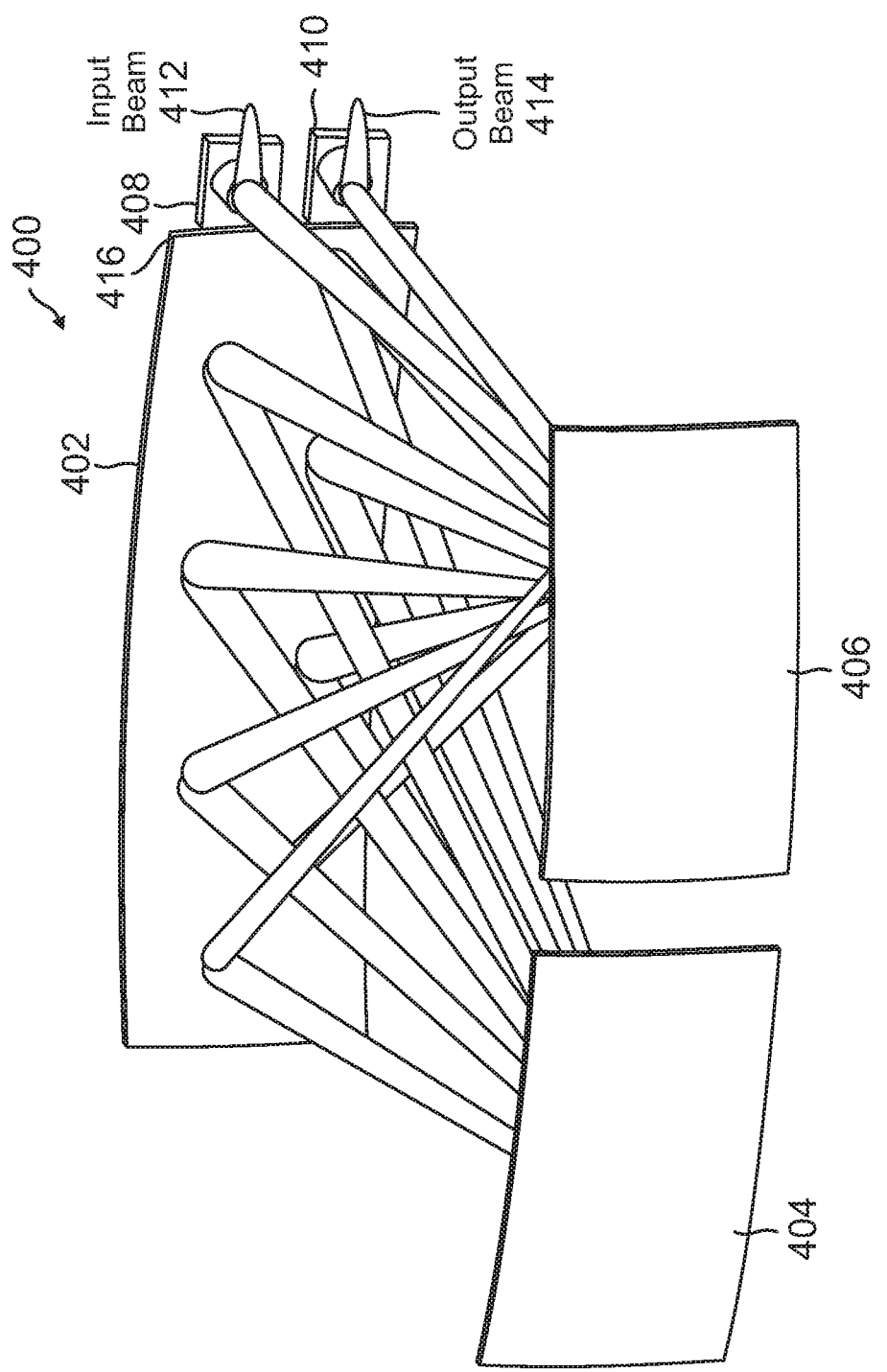
FIG. 4 is a diagram illustrating another example of a multi-pass gas cell including integrated collimating and focusing optical components.

FIG. 4 is a diagram illustrating another example of a multi-pass gas cell 400 in accordance with aspects of the disclosure. In the example shown in FIG. 4, the multi-pass gas cell 400 includes a set of three spherical mirrors 402, 404, and 406, configured as shown in FIG. 2. The multi-pass gas cell 400 further includes a first (or input) optical component 408 optically coupled to receive an input beam (input light) 412 at an optical input of the gas cell 400 and configured to collimate the input light 412 and direct the collimated input light into the gas cell 400 to produce multiple reflections thereof through multiple passes via spherical mirrors 402, 404, and 406. In addition, the multi-pass gas cell 400 includes a second (or output) optical component 410 optically coupled to receive output light 414 resulting from the multiple reflections of the collimated light (e.g., after the multiple passes) and configured to focus the output light 414 towards an optical output of the gas cell 400. The first and second optical components 408 and 410 may include curved mirrors or lenses. For example, the first and second optical component 408 and 410 may include off-axis parabolic mirrors.

The input optical component 408 is integrated with the spherical mirror 402 on a first end 416 thereof. In addition, in the example shown in FIG. 4, the optical component 410 is also integrated with the spherical mirror on the same first end 416 of the spherical mirror 402 as the input optical component 408. Having both optical components (input and output) 408 and 410 integrated on the same end 416 of the spherical mirror 402 may simplify assembly of the multi-pass gas cell 400 with a MEMS module (e.g., a MEMS spectrometer) and light source.

Figure 5:
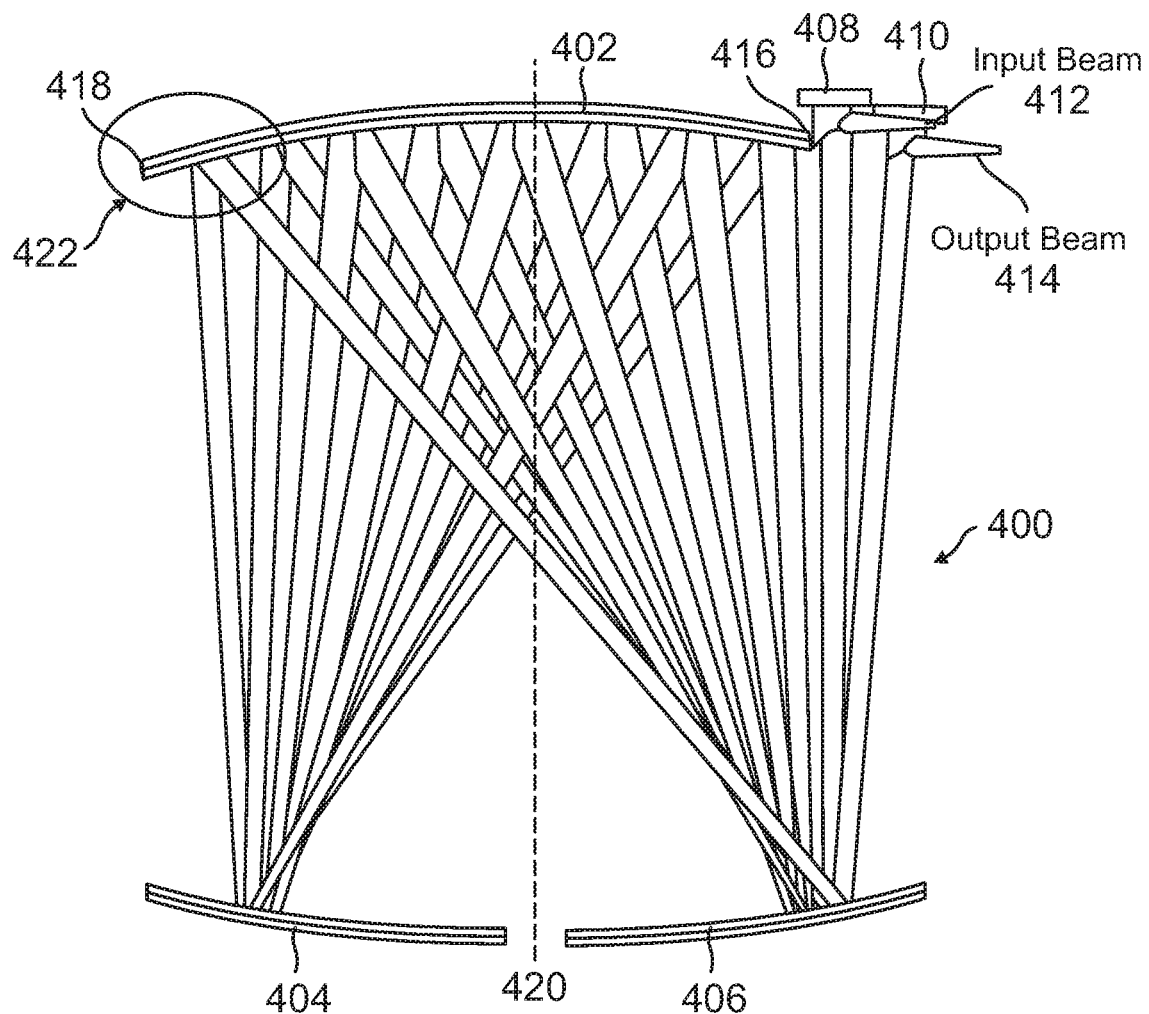
FIG. 5 is a diagram illustrating an elevation view of the multi-pass gas cell of FIG. 4.

In some examples, as shown in the elevation view of FIG. 5, the spherical mirror 402 may include an asymmetrical portion 422 from a line of symmetry 420 of the spherical mirror 402. The asymmetrical portion 422 is on a second end 418 of the spherical mirror 402 that is opposite the first end 416 having the off-axis parabolic mirrors 408 and 410 integrated therewith. The asymmetrical portion 422 enables reflection of the collimated light back into the multi-pass gas cell 400 at the moment the collimated light would typically exit the multi-pass gas cell 400, as indicated in the example shown in FIG. 2. This reflection results in the collimated light exiting from the same side of the multi-pass gas cell 400 as the light enters. Thus, the optical input and optical output are on the same side of the multi-pass gas cell 400.

Figure 6:
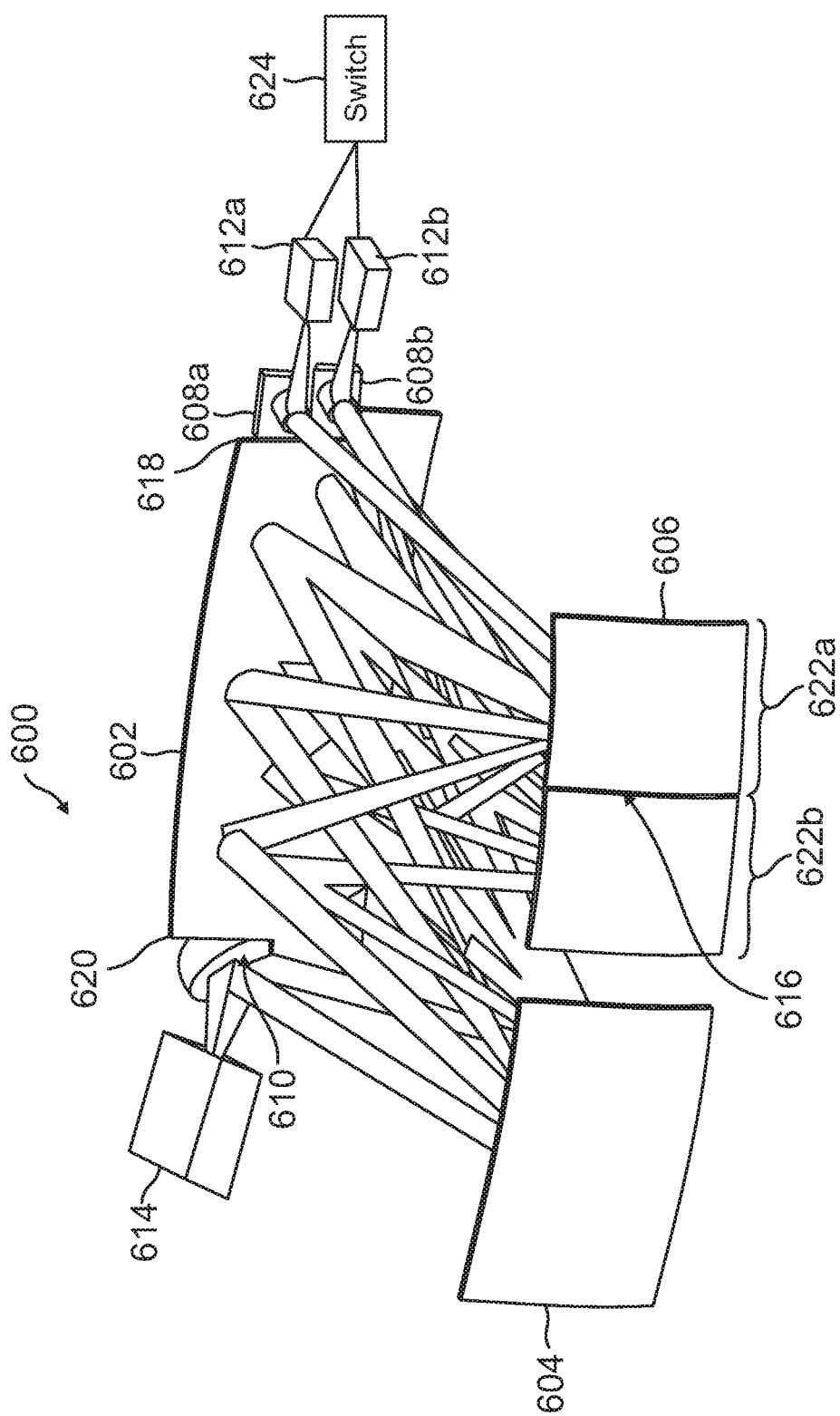
FIG. 6 is a diagram illustrating another example of a multi-pass gas cell including multiple multi-pass optical path lengths.

FIG. 6 is a diagram illustrating another example of a multi-pass gas cell 600 including multiple multi-pass optical path lengths. The different multi-pass optical path lengths may support measurements of different types of gases, each with a different absorption. In the example shown in FIG. 6, the multi-pass gas cell 600 provides two different multi-pass optical path lengths. However, it should be understood that additional multi-pass optical path lengths may be configured using the concepts described herein.

The multi-pass gas cell 600 includes a set of three spherical mirrors 402, 404, and 406, configured as shown in FIG. 2 and/or FIG. 4. The multi-pass gas cell 600 further includes a first input optical component 608a optically coupled to receive a first input beam (first input light) from a first light source 612a at an optical input of the gas cell 600 and configured to collimate the first input light and direct the first collimated input light into the gas cell 600 to produce multiple reflections thereof through multiple passes over a first multi-pass optical path length via spherical mirrors 602, 604, and 606. The multi-pass gas cell 600 also includes a second input optical component 608a optically coupled to receive a second input beam (second input light) from a second light source 612b at the optical input of the gas cell 600 and configured to collimate the second input light and direct the second collimated input light into the gas cell 600 to produce multiple reflections thereof through multiple passes over a second multi-pass optical path length via spherical mirrors 602, 604, and 606.

In addition, the multi-pass gas cell 600 includes an output optical component 610 optically coupled to receive output light resulting from the multiple reflections of each of the first collimated light and the second collimated light (e.g., after the multiple passes) and configured to focus the output light towards a spectrometer 614 (e.g., a MEMS spectrometer) at an optical output of the gas cell 600. Each of the first and second input optical components 608a and 608b is integrated with the spherical mirror 602 on a first end 618 thereof, whereas the output optical component 610 is integrated with the spherical mirror 602 on a second end 620 of the spherical mirror 602 opposite the first end 618. In some examples, the optical components 608a, 608b, and 610 may include curved mirrors or lenses. For example, the optical components 608a, 608b, and 610 may include off-axis parabolic mirrors.

In some examples, the output optical component 610 has a size that is larger than the respective sizes of the input off-optical components 608a and 608b to enable the output optical component 610 to collect the output light coming from each of the two different multi-pass optical path lengths. For example, the size of the larger output optical component 610 may be twice the size of the smaller input optical components 608a and 608b. In an example, the size of the output optical component may be 28 mm and the size of each input optical component 608a and 608b may be 14 mm. In some examples, the total optical power coupled in the two multi-pass optical path lengths may be equal to the total optical power coupled in the single multi-pass optical path length shown in the examples of FIGS. 2 and/or 4. In other words, each multi-pass optical path length may couple half of the optical power of the single multi-pass optical path length shown in the examples of FIGS. 2 and/or 4.

Figure 7:
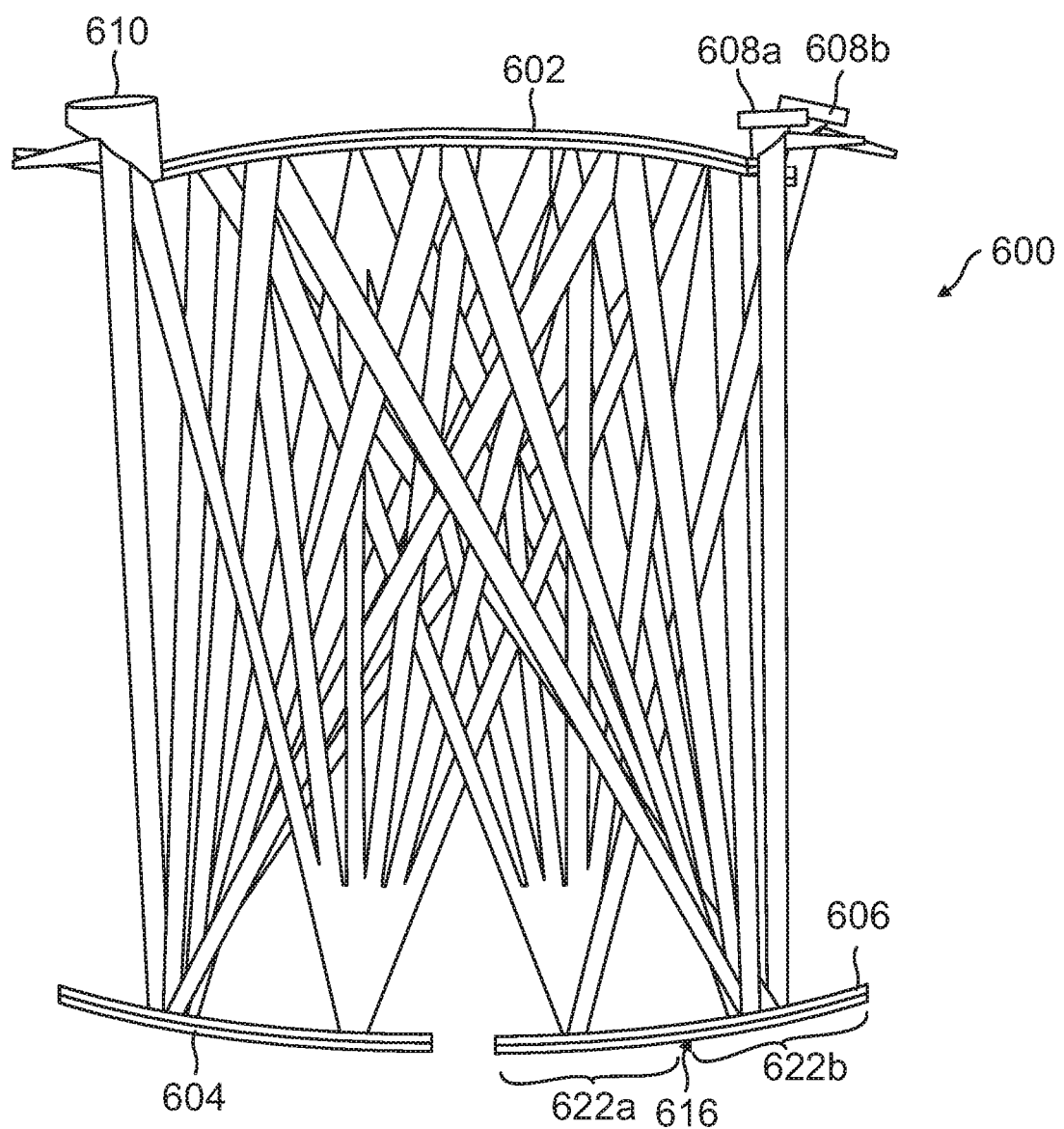
FIG. 7 is a diagram illustrating an elevation view of the multi-pass gas cell of FIG. 6.

In the example shown in FIG. 6, the third spherical mirror 606 includes a discontinuity 616 that produces a first part 622a of the third spherical mirror 606 and a second part 622b of the third spherical mirror 606. The first part 622a and the second part 622b each comprise a different respective tilt to form the different multi-pass optical path lengths within the multi-pass gas cell 600. For example, as can be seen in FIG. 6 and the elevation view of FIG. 7, the first part 622a of the third spherical mirror 606 produces a first multi-pass path length including a first number of reflections of the first collimated light and the second part 622b of the third spherical mirror 606 produces a second multi-pass path length including a second number of reflections of the second collimated light. Here, the first number of reflections is different than the second number of reflections to create the different multi-pass optical path lengths.

Figure 8:
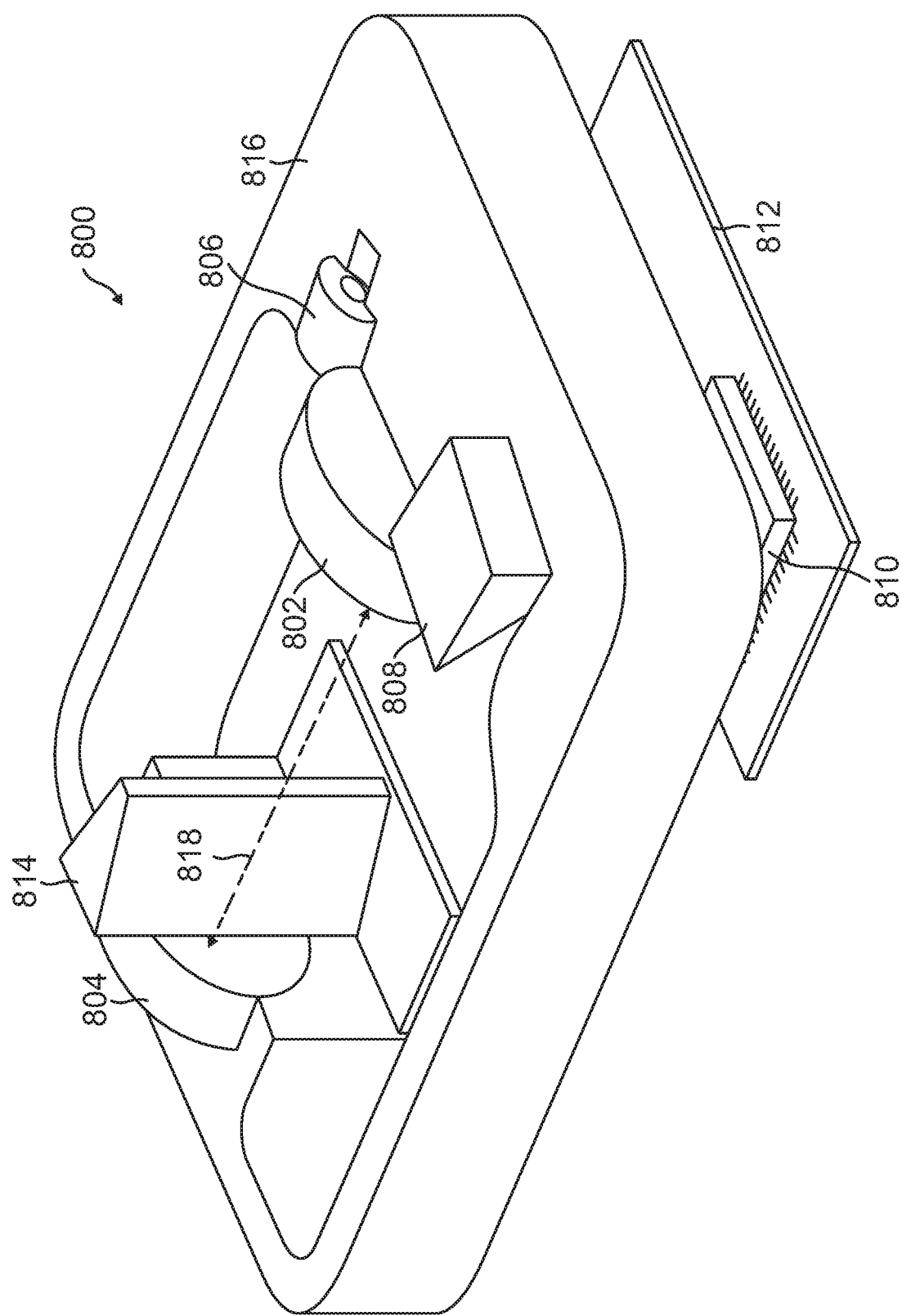
FIG. 8 is a diagram illustrating another example of a multi-pass gas cell including integrated collimating and focusing optical components

FIG. 8 is diagram illustrating another example of a multi-pass gas cell 800 in accordance with aspects of the disclosure. The multi-pass gas cell 800 includes a first substrate 816 and a second substrate 812. The first substrate 816 may be composed of any suitable material, such as plastic, glass, metal, dielectric, or semiconductor material. The second substrate 812 may be, for example, a printed circuit board that includes an optical core module 810 attached thereto. The optical core module 810 may include a spectrometer, a processor, a memory, and other suitable components for analyzing gases.

In the example shown in FIG. 8, the first substrate 816 include a set of reflectors 802 and 804 and optical components 806 and 808. In some examples, the set of reflectors 802 and 804 includes two concave mirrors. The first concave mirror 802 has a first radius of curvature, whereas the second concave mirror 804 has a second radius of curvature that is twice the first radius of curvature. In addition, a distance 818 between the first concave mirror 802 and the second concave mirror 804 is equal to the second radius of curvature. Unlike conventional White gas cells, there is no tilting in any mirror 802 and 804, which results in a perfect symmetric gas cell 800. The symmetry produces the same angles for the source and the detector (with respect to the symmetry line of the mirrors 802 and 804). Due to the different radii of curvature in the mirrors 802 and 804, the light reflects back and forth in the cell 800 without affecting beam collimation since the total distance traveled by the light in the cell 800 is small compared to conventional White gas cells.

In some examples, the first optical component (e.g., an input optical component) 806 includes a curved mirror or lens, such as an off-axis parabolic mirror, for collimating input light and directing the input light towards the second concave mirror 804 for multiple reflections thereof between the concave mirrors 802 and 804. The second optical component (e.g., an output optical component) 808 may be a right angle mirror optically coupled (e.g., positioned within the gas cell 800) to receive the output light from the second concave mirror 804 and configured to focus the output light onto the optical core module 810. The output optical component 808 may further be curved to collimate the output light as well as change the optical axis ninety degrees. The first and second optical components 806 and 808 may be integrated with the first concave mirror 802 on respective ends thereof.

In the example shown in FIG. 8, the first and second concave mirrors 802, along with the first and second optical components 806 and 808, are fabricated within the first substrate 816. For example, the concave mirrors 802 and 804 and collimating/focusing optical components 806 and 808 may be fabricated monolithically and in a self-aligned manner within the substrate 816 using injection molded optics, etching (e.g., of a semiconductor substrate), or other suitable fabrication technique.

Figure 9:
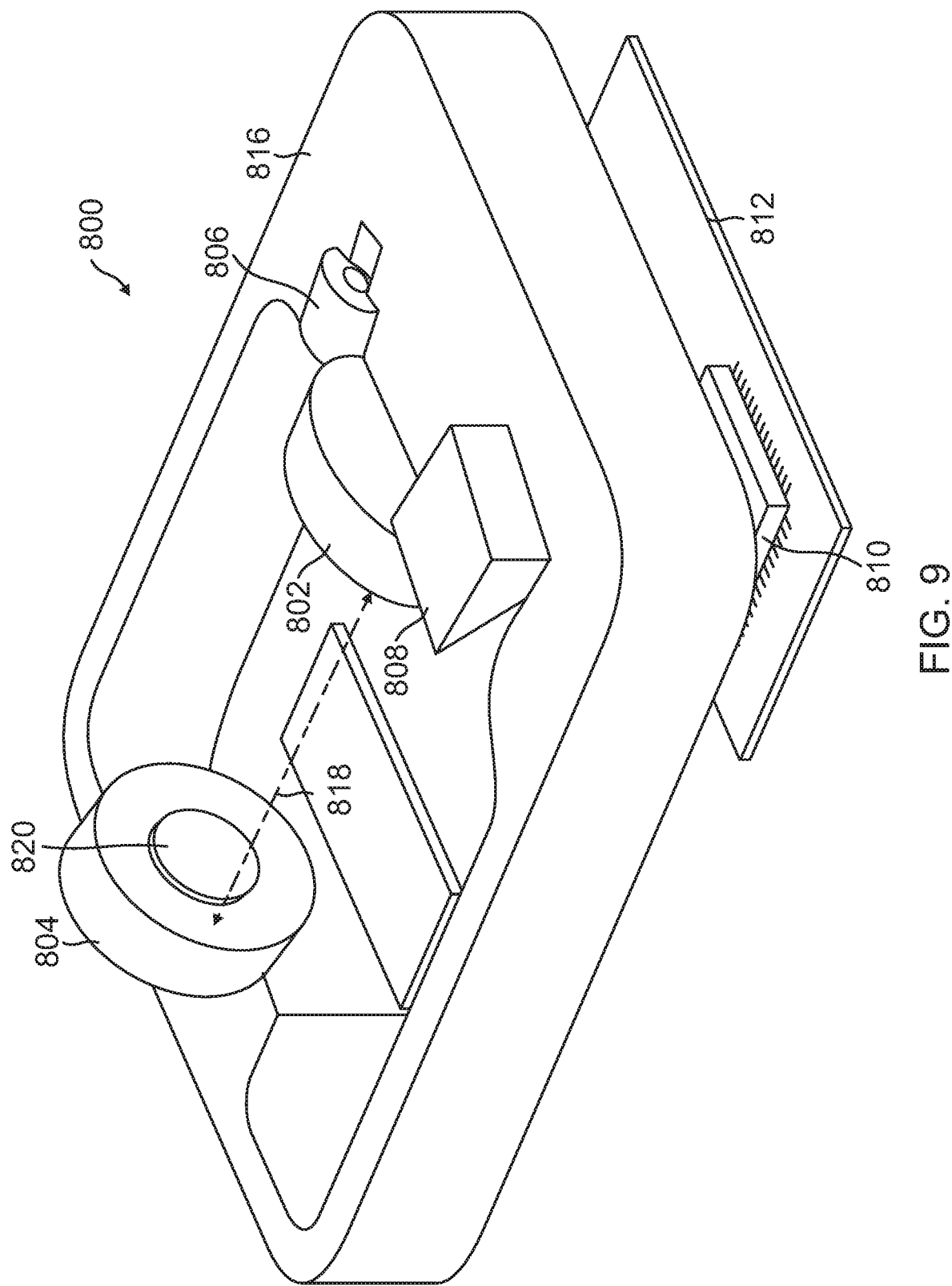
FIG. 9 is a diagram illustrating another example of a multi-pass gas cell including integrated collimating and focusing optical components.

The gas cell structure shown in FIG. 8 may suffer from stray light traveling from the input optical component 806 to the output optical component via a single reflection off of the second concave mirror 804. To remove stray light from the output, in one example, an absorber 814 may be inserted into the gas cell 800 and positioned between the concave mirrors 802 and 804. In some examples, the absorber 814 may be integrated with the second concave mirror 804 and fabricated within the first substrate 816. In other examples, as shown in FIG. 9, the second concave mirror 804 may include an absorbing area 820 configured to block stray light from reaching the output. For example, the second concave mirror 804 can be fabricated to include a non-metallized portion forming the absorbing area 820.

Figure 10:
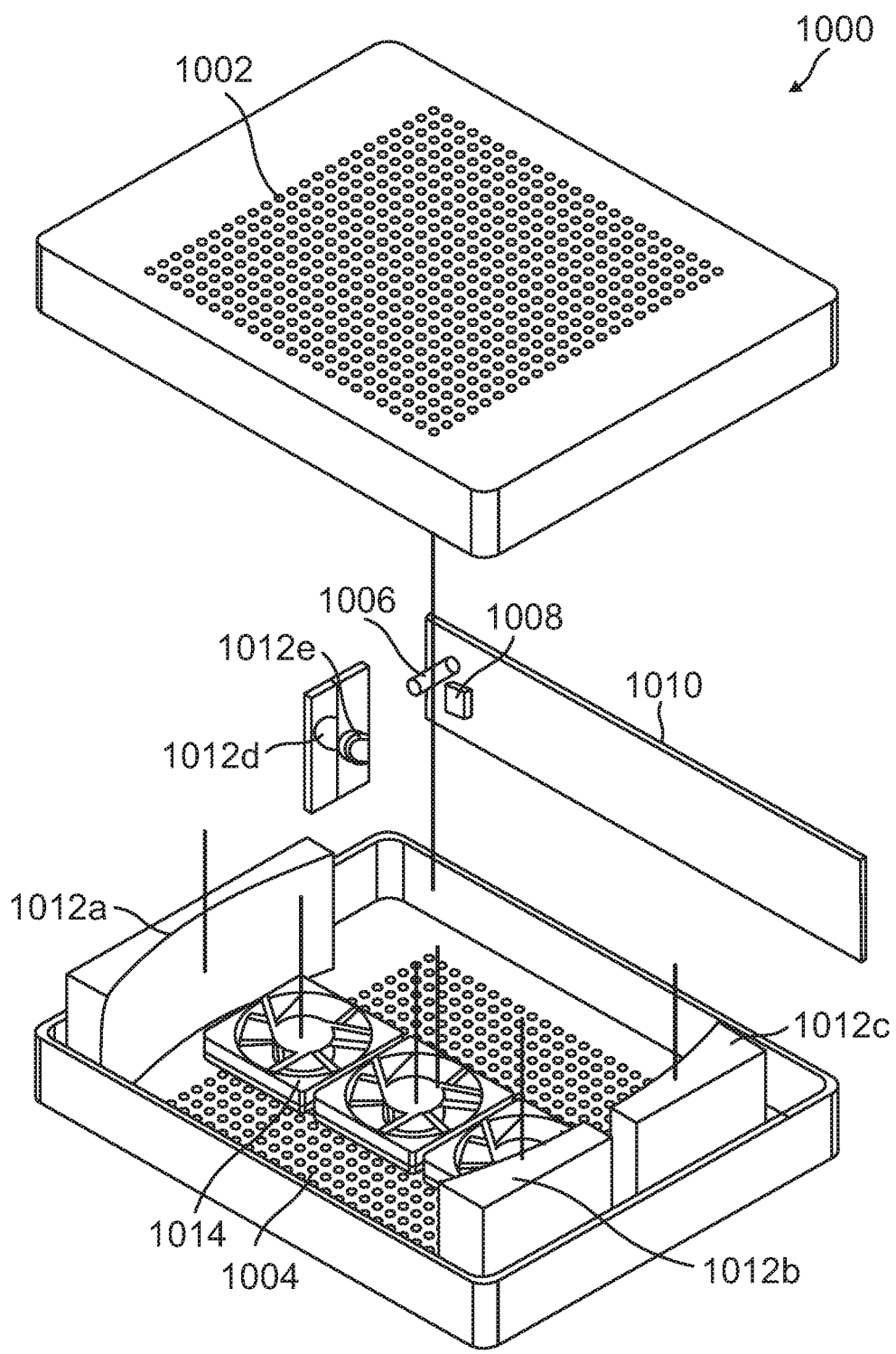
FIG. 10 is an exploded view of a multi-pass gas cell.

FIG. 10 is an exploded view of a multi-pass gas cell 1000 that provides compatibility with MEMS spectrometers for miniature gas analyzer applications. The multi-pass gas cell 1000 of FIG. 10 will further be described with reference to the different views of the multi-pass gas cell 1000 shown in FIGS. 11A-11D. The multi-pass gas cell 1000 includes an enclosure formed of an enclosure top 1002 and an enclosure bottom 1004. In addition, the multi-pass gas cell 1000 includes a light source 1006, a MEMS spectrometer 1008, mirrors 1012a-1012e, and a fan 1014. The light source 1006 and MEMS spectrometer 1008 may be attached to a printed circuit board 1010 or other suitable substrate that may be inserted into the multi-pass gas cell 1000.

Figure 11A:
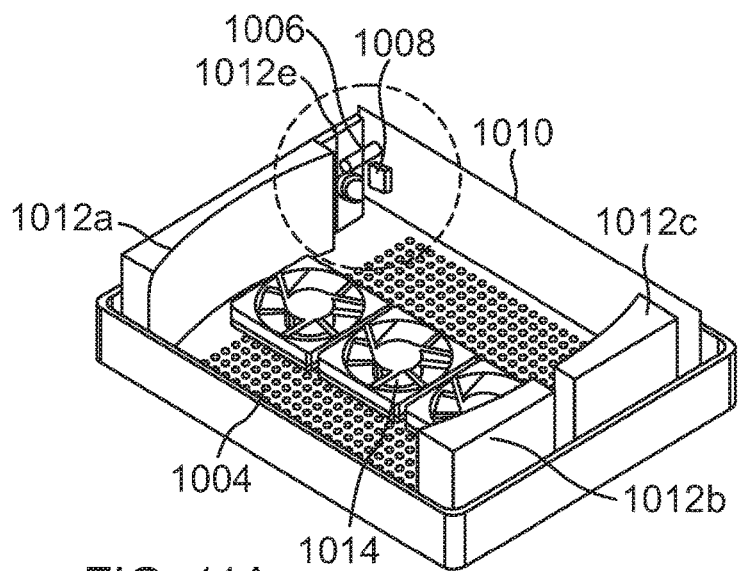
FIGS. 11A-11D are different views of the multi-pass gas cell of FIG. 10.
Figure 11B:
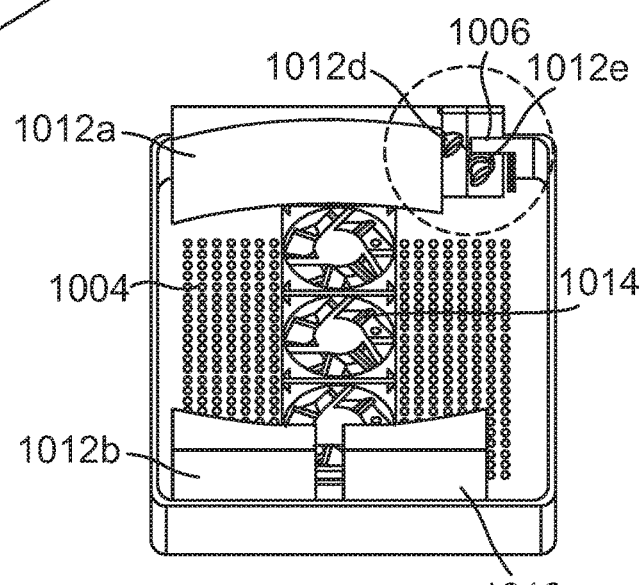
Figure 11C:
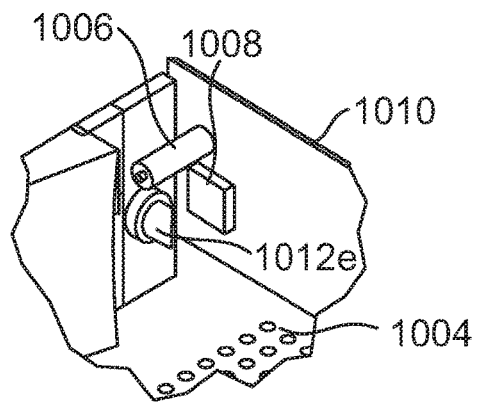
Figure 11D:
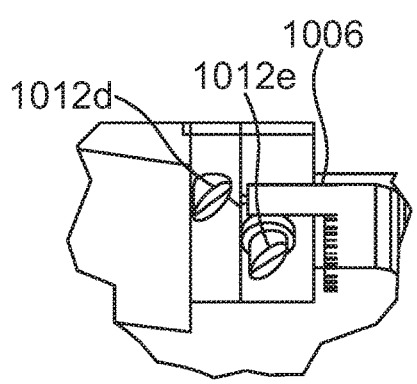

The mirror structure may be similar to the structure shown in FIGS. 4 and 5. For example, as shown in FIGS. 10, 11A and 11B, the mirrors 1012 may include a set of three spherical mirrors 1012a, 1012b, and 1012c, a collimating input mirror 1012d and a focusing output mirror 1012e. As shown in FIGS. 11A-11D, the input mirror 1012d is optically coupled to receive input light from the light source 1006 and configured to collimate the input light and direct the collimated input light to the spherical mirror 1012c for multiple reflections of the collimated light between spherical mirror 1012a and spherical mirrors 1012b and 1012c. Output mirror 1012e is optically coupled to receive output light from spherical mirror 1012b and to focus the output light towards the MEMS spectrometer 1008.

As in FIGS. 4 and 5, the input and output mirrors 1012d and 1012e are located on the same side of the large spherical mirror 1012a to facilitate alignment and assembly with the light source 1006 and MEMS spectrometer 1008. In addition, mirrors 1012d and 1012e are integrated with the spherical mirror 1012a. For example, the mirrors 1012a, 1012e and 1012e may be fabricated within the same substrate using any suitable fabrication technique.

In the example shown in FIGS. 10, 11A, and 11B, the fan 1014 may provide a mechanism for circulating gas from outside the enclosure 1002/1004 to inside the enclosure 1002/1004. The circulation may lead to higher pressure inside the enclosure that helps in detecting gas traces with low concentration. In other examples, a heating element or a mechanical pump may be used instead of the fan 1014 to provide the gas circulation. In still other examples, the gas may be directed into and out of the multi-pass gas cell 1000 via tubing (not shown). In some examples, various components (e.g., the enclosure 1002/1004 and other suitable components) of the multi-pass gas cell 1000 may be nickel-plated to prevent corrosion that may result from exposure to some gases. In some examples, various components (e.g., the enclosure 1002/1004 and other suitable components) of the multi-pass gas cell 1000 may be anti-adsorption coated to prevent the adsorption of the gas to the surfaces that may lead to in accurate prediction of the current or subsequent gas concentration.

Figure 12:
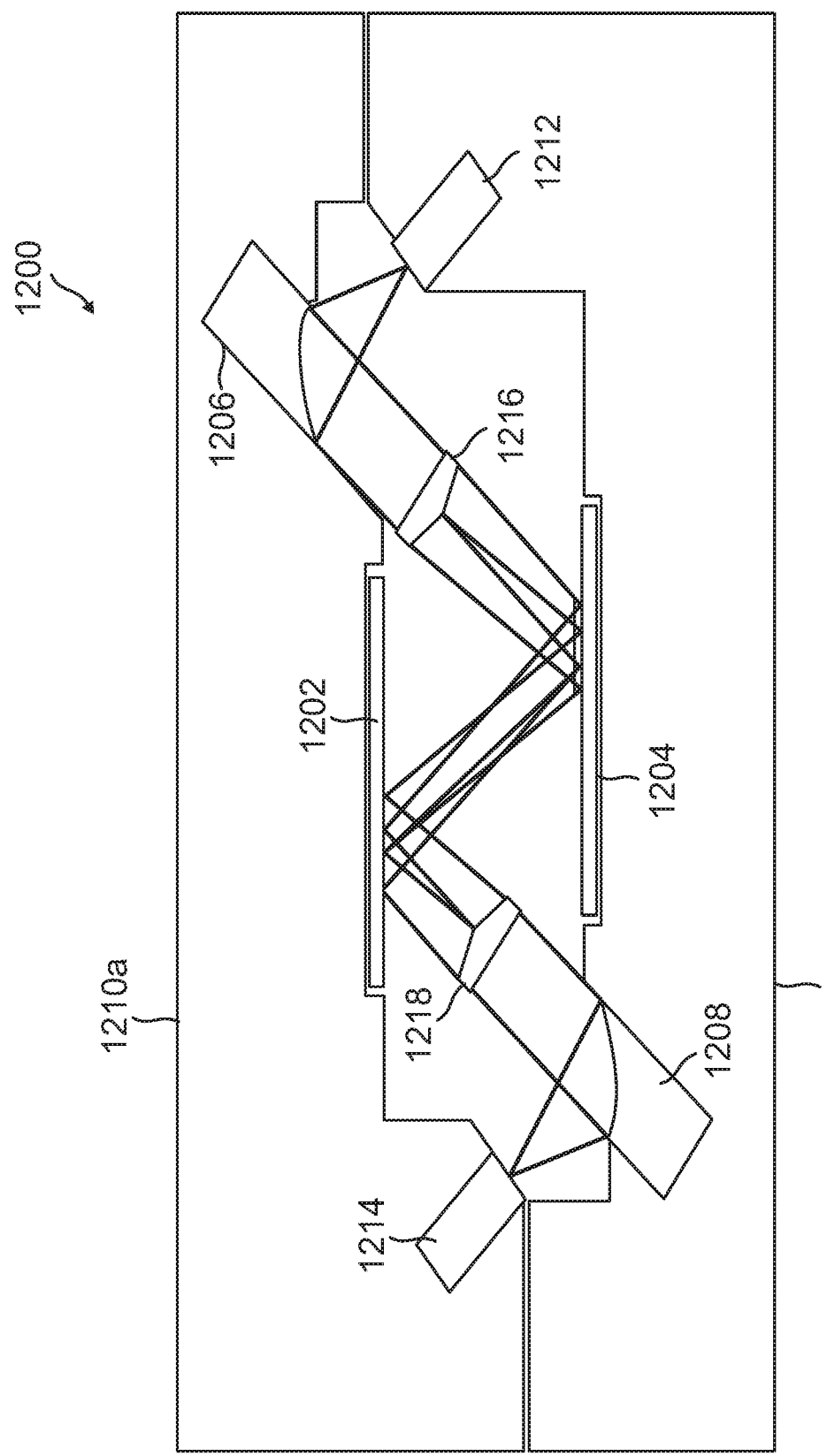
FIG. 12 is a diagram illustrating another example of a multi-pass gas cell including integrated collimating and focusing optical elements.

FIG. 12 is a diagram illustrating another example of a multi-pass gas cell 1200 in accordance with aspects of the disclosure. The multi-pass gas cell 1200 includes a set of two reflectors 1202 and 1204. In the example shown in FIG. 12, each reflector 1202 and 1204 is a flat mirror. The multi-pass gas cell 1200 further includes a first (or input) optical component 1206 and a second (or output) optical component 1208. The first and second optical components 1206 and 1208 may include curved mirrors or lenses. For example, the first and second optical component 1206 and 1208 may include off-axis parabolic mirrors.

The input optical component 1206 is integrated with flat mirror 1202 and the output optical component 1208 is integrated with flat mirror 1204. For example, the input optical component 1206 may be fabricated within the same substrate 1210*a* as flat mirror 1202, whereas the output optical component 1208 may be fabricated within the same substrate 1210*b* as flat mirror 1204. In some examples, the substrates 1210*a* and 1210*b* may be separate halves of an optical mold including the multi-pass gas cell 1000 that may be produced by injection molding. In other examples, the substrates 1210*a* and 1210*b* may be etched in a semiconductor substrate using 3D micromachining techniques.

In addition, the multi-pass gas cell 1200 includes a first optical Bessel component 1216 and a second optical Bessel component 1218. The first and second optical Bessel components 1216 and 1218 may be utilized to decrease the losses due to diffraction without using spherical mirrors. In some examples, the first and second optical Bessel components may include axicon lenses, annular apertures, or conical reflectors.

In an example, the input optical component 1206 is optically coupled to receive an input beam (input light) from a light source 1212 and configured to collimate the input light and direct the collimated input light to the first optical Bessel component 1216. The first optical Bessel component 1216 is optically coupled to receive the collimated input light and configured to generate input Bessel beams for propagation inside the multi-pass gas cell including multiple reflections between the flat mirrors 1202 and 1204. The second optical Bessel component 1218 is optically coupled to receive output Bessel beams resulting from the multiple reflections and configured to generate output collimated light as output light. The output optical component 1208 is optically coupled to receive the output light from the second optical Bessel component 1218 and configured to focus the output light towards a spectrometer 1214 (e.g., a MEMS spectrometer).

Figure 13:
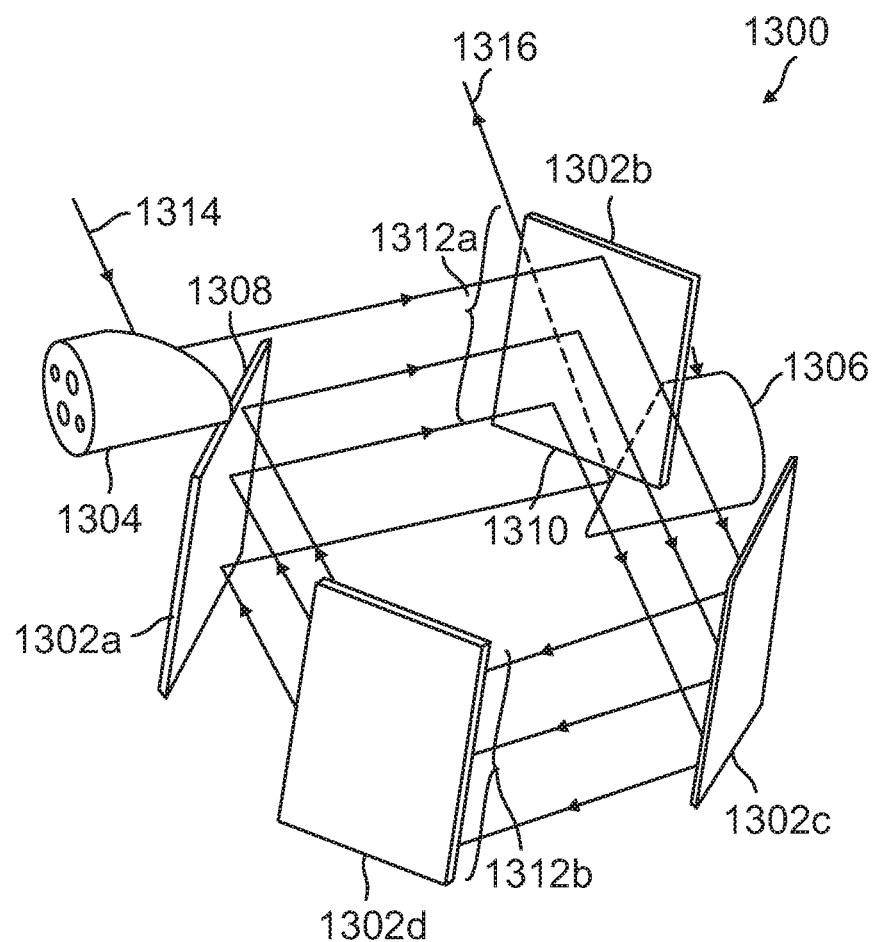
FIG. 13 is a diagram illustrating another example of a multi-pass gas cell including integrated collimating and focusing optical components.

FIG. 13 is a diagram illustrating another example of a multi-pass gas cell 1300 in accordance with aspects of the disclosure. In the example shown in FIG. 13, the multi-pass gas cell 1300 includes a set of four reflectors 1302*a*, 1302*b*, 1302*c*, and 1302*d*. In the example shown in FIG. 13, each reflector 1302*a*, 1302*b*, 1302*c*, and 1302*c* is a flat mirror. In other examples, the reflectors 1302*a*, 1302*b*, 1302*c*, and 1302*d* may be cylindrical mirrors. For example, in larger gas cells 1300, cylindrical mirrors may decrease beam divergence. Two of the four reflectors (e.g., reflectors 1302*a* and 1302*b*) may be shorter than the other two reflectors (e.g., reflectors 1302*c* and 1302*d*) to enable light to enter and exit the gas cell 1300. For example, reflectors 1302*a* and 1302*b* may have a first length 1312*a* and reflectors 1302*c* and 1302*d* may have a second length 1312*b* greater than the first length.

The multi-pass gas cell 1300 further includes a first (or input) optical component 1304 and a second (or output) optical component 1306. The first and second optical components 1304 and 1306 may include curved mirrors or lenses. For example, the first and second optical component 1304 and 1306 may include off-axis parabolic mirrors.

The input optical component 1304 may be integrated with flat mirror 1302*a* and the output optical component 1306 may be integrated with flat mirror 1302*c*. For example, the input optical component 1304 may be fabricated within the same substrate (not shown, for simplicity) as flat mirrors 1302*a* and 1302*b*, whereas the output optical component 1306 may be fabricated within the same substrate (not shown, for simplicity) as flat mirrors 1302*c* and 1302*d*. In some examples, the substrates may be separate halves of an optical mold including the multi-pass gas cell 1300 that may be produced by injection molding.

In an example, the input optical component 1304 is integrated on a top portion 1308 of the first flat mirror 1302*a* (e.g., having a shorter length). The input optical component 1304 is further optically coupled (e.g., positioned on the first flat mirror 1302*a*) to receive input light 1314, collimate the input light and direct the collimated light towards the second flat mirror 1302*b* at an angle selected to produce a spiral multi-pass optical path of the collimated light between the second flat mirror 1302*b*, the third flat mirror 1302*c*, the fourth flat mirror 1302*d*, and the first flat mirror 1302*a*. The output optical component 1306 is integrated on a bottom portion 1310 of the second flat mirror 1302*c* (e.g., having a shorter length). The output optical component 1306 is optically coupled (e.g., positioned on the bottom portion of the second flat mirror 1302*c*) to receive the output light 1316 from the fourth flat mirror 1302*d* and to focus the output light 1316 towards an optical output of the gas cell 1300.

Figure 14:
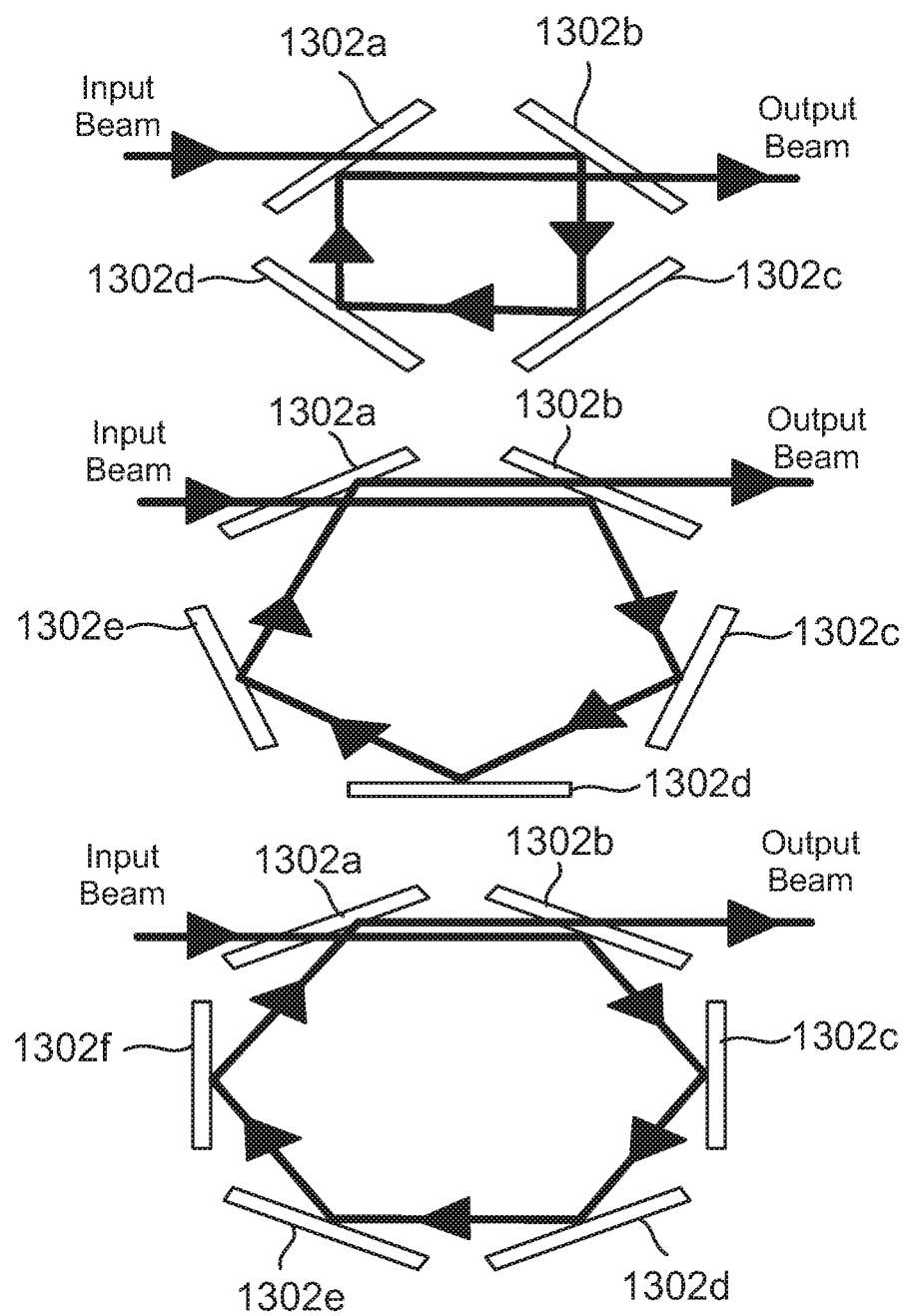
FIG. 14 is a diagram illustrating exemplary configurations of reflectors in the multi-pass gas cell of FIG. 13.

In some examples, the multi-pass gas cell 1300 may include more than four reflectors 1302*a*-1302*d*. For example, as shown in FIG. 14, the multi-pass gas cell may be designed with four reflectors 1302*a*-1302*d*, five reflectors 1302*a*-1302*e*, or six reflectors 1302*a*-1302*f*. In each of the examples, an input beam is received at an optical input of the multi-pass gas cell by the first reflector 1302*a* (e.g., via an input collimating optical component) and an output beam is directed by the second reflector 1302*b* (e.g., via an output focusing optical component) towards an optical output of the multi-pass gas cell. Therefore, as in the example shown in FIG. 13, each of the first and second reflectors 1302*a* and 1302*b* has a shorter length than the other reflectors 1302*c*-1302*f* to direct the light into and out of the gas cell.

FIG. 15 is a diagram illustrating another example of a multi-pass gas cell 1500 in accordance with aspects of the disclosure. FIG. 15 includes a side view and a perspective view of a multi-pass gas cell 1500 including an optical mold 1502 (e.g., an enclosure) that includes a light source 1504, an optical core module 1506, and various optical devices (e.g., input/output optical components and reflectors for producing the multiple reflections, as shown in any of FIGS. 2-14 above). The optical devices may be internal to the optical mold 1502, and as such, are not shown in FIG. 15, for simplicity. The optical mold 1502 may be fabricated, for example, using injection molded optics technology to enable mass production of the multi-pass gas cell 1500 that results in self-aligned optical devices. With injection molding, the optical mold 1502 may be fabricated as two parts that are nearly symmetric with respect to one or more axes of symmetry.

The optical core module 1506 may include, for example, a MEMS spectrometer. In addition, the light source 1504 may include, for example, a light-emitting diode (LED) or filament source. In the example shown in FIG. 15, the multi-pass gas cell 1500 may further include an element 1508 configured to absorb or block water content in the gas. In some examples, the element 1508 may include a filter or other suitable structure for absorbing or blocking humidity or water content in the gas.

Within the present disclosure, the word "exemplary" is used to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure.

One or more of the components, steps, features and/or functions illustrated in FIGS. 1-15 may be rearranged and/or combined into a single component, step, feature or function or embodied in several components, steps, or functions. Additional elements, components, steps, and/or functions may also be added without departing from novel features disclosed herein. The apparatus, devices, and/or components illustrated in FIGS. 1-15 may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A multi-pass gas cell, comprising:
   a first optical component optically coupled to receive input light at an optical input of the multi-pass gas cell and configured to collimate the input light to produce collimated light;
   a set of two or more reflectors optically coupled to receive the collimated light and configured to reflect the collimated light within the multi-pass gas cell to produce multiple reflections of the collimated light; and
   a second optical component optically coupled to receive output light resulting from the multiple reflections of the collimated light and configured to focus the output light towards an optical output of the multi-pass gas cell;
   wherein the first optical component and the second optical component are positioned apart from one another and different than the set of two or more reflectors;
   wherein the first optical component and the second optical component are integrated with a single reflector of the set of two or more reflectors.

2. The multi-pass gas cell of claim 1, wherein the set of two or more reflectors comprises at least three curved reflectors.

3. The multi-pass gas cell of claim 1, wherein the first optical component and the second optical component comprise curved mirrors or lenses.

4. The multi-pass gas cell of claim 1, wherein:
   the set of two or more reflectors comprise a first spherical mirror, a second spherical mirror, and a third spherical mirror, each comprising a same radius of curvature that is equal to a distance between the first spherical mirror and each of the second spherical mirror and the third spherical mirror;
   the first spherical mirror is positioned on a first side of the multi-pass gas cell and both the second spherical mirror and the third spherical mirror are positioned on a second side of the multi-pass gas cell opposite the first side;
   an angle between the second spherical mirror and the third spherical mirror is selected to maintain the collimated light inside the multi-pass gas cell; and
   the first spherical mirror comprises the single reflector.

5. The multi-pass gas cell of claim 4, wherein the first spherical mirror, the second spherical mirror and the third spherical mirror each comprise a constant thickness.

6. The multi-pass gas cell of claim 4, wherein the first optical component is integrated on a first end of the first spherical mirror and the second optical component is integrated on a second end of the first spherical mirror opposite the first end.

7. The multi-pass gas cell of claim 6, further comprising:
   a third optical component optically coupled to receive additional input light at the optical input of the multi-pass gas cell and configured to collimate the additional input light to produce additional collimated light for reflection of the additional collimated light between the first spherical mirror and each of the second spherical mirror and the third spherical mirror, wherein the third optical component is further integrated on the first end of the first spherical mirror.

8. The multi-pass gas cell of claim 7, wherein the second spherical mirror comprises a discontinuity that produces a first part of the second spherical mirror and a second part of the second spherical mirror, wherein the first part and the second part each comprise a different respective tilt to form different respective multi-pass optical path lengths within the multi-pass gas cell.

9. The multi-pass gas cell of claim 8, wherein the first part of the second spherical mirror produces a first multi-pass optical path length comprising a first number of reflections of the collimated light and the second part of the second spherical mirror produces a second multi-pass optical path length comprising a second number of reflections of the additional collimated light, wherein the first number of reflections is different than the second number of reflections.

10. The multi-pass gas cell of claim 7, wherein the first optical component, the second optical component, and the third optical component comprise curved mirrors or lenses, and wherein a size of the second optical component is greater than respective sizes of each of the first optical component and the third optical component.

11. The multi-pass gas cell of claim 7, further comprising:
two light sources; and
a switch coupled to the two light sources and configured to switch between the two light sources.

12. The multi-pass gas cell of claim 1, wherein the first optical component and the second optical component are both integrated on a first end of the single reflector such that the optical input and the optical output are located on the first end of the single reflector.

13. The multi-pass gas cell of claim 12, wherein the single reflector comprises an asymmetrical portion on a second end thereof that is opposite to the first end to enable reflection of the collimated light back into the multi-pass gas cell.

14. The multi-pass gas cell of claim 1, wherein:
the set of two or more reflectors comprise a first concave mirror and a second concave mirror, the first concave mirror comprising the single reflector;
the first concave mirror comprises a first radius of curvature and the second concave mirror comprises a second radius of curvature that is twice the first radius of curvature; and
a distance between the first concave mirror and the second concave mirror is equal to the second radius of curvature.

15. The multi-pass gas cell of claim 14, further comprising:
an absorber optically coupled to prevent stray light of the collimated light from reaching the optical output of the multi-pass gas cell.

16. The multi-pass gas cell of claim 15, wherein the absorber is positioned between the first concave mirror and the second concave mirror.

17. The multi-pass gas cell of claim 15, wherein the absorber comprises an absorbing area on the second concave mirror.

18. The multi-pass gas cell of claim 16, wherein the first optical component and the second optical component comprise right angle mirrors, curved mirrors or lenses.

19. The multi-pass gas cell of claim 1, wherein the first optical component is integrated with a first reflector of the set of two or more reflectors and the second optical component is integrated with a second reflector of the set of two or more reflectors.

20. The multi-pass gas cell of claim 19, wherein:
the set of two or more reflectors comprise at least a first mirror, a second mirror, a third mirror, and a fourth mirror;
the first optical component is integrated with the first mirror; and
the second optical component is integrated with the second mirror.

21. The multi-pass gas cell of claim 20, wherein the first optical component and the second optical component comprise curved mirrors or lenses.

22. The multi-pass gas cell of claim 20, wherein each of the first mirror, the second mirror, the third mirror, and the fourth mirror comprise flat mirrors or cylindrical mirrors.

23. The multi-pass gas cell of claim 20, wherein the first mirror and the second mirror each comprise a first length and the third mirror and the fourth mirror each comprise a second length greater than the first length.

24. The multi-pass gas cell of claim 23, wherein:
the first optical component is integrated on a top portion of the first mirror to direct the collimated light towards the second mirror at an angle selected to produce a spiral multi-pass optical path of the collimated light between the second mirror, the third mirror, the fourth mirror, and the first mirror; and
the second optical component is integrated on a bottom portion of the second mirror to receive the output light reflected from the first mirror and to focus the output light toward the optical output.

25. The multi-pass gas cell of claim 19, wherein the set of two or more reflectors comprise a first flat mirror and a second flat mirror, the first optical component is integrated with the first flat mirror and the second optical component is integrated with the second flat mirror, and further comprising:
a first optical Bessel component optically coupled to receive the collimated light from the first optical component and configured to generate input Bessel beams for propagation inside the multi-pass gas cell comprising the multiple reflections between the first flat mirror and the second flat mirror; and
a second optical Bessel component optically coupled to receive output Bessel beams resulting from the multiple reflections and configured to generate output collimated light as the output light received by the second optical component.

26. The multi-pass gas cell of claim 25, wherein:
the first optical component and the second optical component comprise curved mirrors or lenses; and
the first optical Bessel component and the second optical Bessel component comprise axicon lenses, annular apertures, or conical reflectors.

27. The multi-pass gas cell of claim 1, further comprising:
an enclosure configured to receive a gas, wherein the set of two or more reflectors, the first optical component and the second optical component are contained within the enclosure.

28. The multi-pass gas cell of claim 27, wherein the enclosure, the set of two or more reflectors, the first optical component, and the second optical component are fabricated within a same substrate using injection molded optics.

29. The multi-pass gas cell of claim 27, further comprising:
a spectrometer; and
a light source, wherein the spectrometer and the light source are assembled inside the enclosure.

30. The multi-pass gas cell of claim 27, further comprising:
a circulation unit configured to circulate the gas from outside the enclosure to inside the enclosure.

31. The multi-pass gas cell of claim 27, further comprising:
an element configured to absorb or block water content in the gas.

* * * * *